(12) United States Patent
Blackburn et al.

(10) Patent No.: US 8,154,726 B2
(45) Date of Patent: Apr. 10, 2012

(54) OPTICAL ANALYSIS SYSTEM AND METHOD FOR REAL TIME MULTIVARIATE OPTICAL COMPUTING

(75) Inventors: John C. Blackburn, Charleston, SC (US); Robert P. Freese, Pittsboro, NC (US); David L. Perkins, Irmo, SC (US)

(73) Assignee: Halliburton Energy Services, Inc., Houston, TX (US)

( * ) Notice: Subject to any disclaimer, the term of this patent is extended or adjusted under 35 U.S.C. 154(b) by 610 days.

(21) Appl. No.: 12/094,462

(22) PCT Filed: Nov. 27, 2006

(86) PCT No.: PCT/US2006/045357
§ 371 (c)(1),
(2), (4) Date: Oct. 6, 2008

(87) PCT Pub. No.: WO2007/064575
PCT Pub. Date: Jun. 7, 2007

(65) Prior Publication Data
US 2009/0097024 A1    Apr. 16, 2009

Related U.S. Application Data

(60) Provisional application No. 60/740,078, filed on Nov. 28, 2005.

(51) Int. Cl.
*G01N 21/25* (2006.01)
(52) U.S. Cl. ............................ 356/416; 356/300
(58) Field of Classification Search ............... 356/416, 356/300–334, 450–451; 250/339.09, 339.06, 250/339.11, 341.8, 341.1, 200, 216, 226; 398/196, 186, 187
See application file for complete search history.

(56) References Cited

U.S. PATENT DOCUMENTS 3,717,078 A    2/1973    Ogura
(Continued)

FOREIGN PATENT DOCUMENTS

EP    1969326 A1    9/2008
(Continued)

OTHER PUBLICATIONS

U.S. Appl. No. 11/581,270, filed Mar. 2, 2007, Freese et al.
(Continued)

*Primary Examiner* — Tri T Ton
(74) *Attorney, Agent, or Firm* — Haynes and Boone, LLP

(57) ABSTRACT

An optical analysis system and method for determining information carried by light include a multivariate optical element disposed in the system to receive a source light from an illumination source; filtering the source light through a spectral element in the optical element analysis system; reflecting the filtered light through an inner region of a cavity in a first direction of a sample to be measured, the cavity defining a second region disposed about the inner region; focusing the reflected light proximate the sample; reflecting the focused light from the sample through the second region in a second direction of a beamsplitter, the light being reflected from the sample carrying data from the sample; splitting the sample carrying light with the beamsplitter into a first light and a second light; optically filtering the data of the first light with the multivariate optical element into an orthogonal component; directing the first light filtered by the multivariate optical element onto a first photodetector; directing the second light onto a second photodetector; and comparing the orthogonal component to information present in the second light to determine a property of the sample.

41 Claims, 2 Drawing Sheets

U.S. PATENT DOCUMENTS

| | | |
|---|---|---|
| 3,761,724 A | 9/1973 | Dennis |
| 4,499,378 A | 2/1985 | Miyatake et al. |
| 4,607,914 A | 8/1986 | Fienup |
| 4,687,337 A | 8/1987 | Stewart et al. |
| 4,704,536 A | 11/1987 | Sugiyama et al. |
| 4,891,574 A | 1/1990 | Nagaya et al. |
| 4,981,332 A | 1/1991 | Smith |
| 5,071,526 A | 12/1991 | Pletcher et al. |
| 5,090,807 A | 2/1992 | Tai |
| 5,103,340 A | 4/1992 | Dono et al. |
| 5,137,364 A | 8/1992 | McCarthy |
| 5,150,236 A | 9/1992 | Patel |
| 5,223,715 A | 6/1993 | Taylor |
| 5,259,381 A | 11/1993 | Cheung et al. |
| 5,406,082 A | 4/1995 | Pearson et al. |
| 5,504,332 A | 4/1996 | Richmond et al. |
| 5,622,868 A | 4/1997 | Clarke et al. |
| 5,641,962 A | 6/1997 | Perry et al. |
| 5,710,655 A | 1/1998 | Rumbaugh et al. |
| 5,734,098 A | 3/1998 | Kraus et al. |
| 5,737,076 A | 4/1998 | Glaus et al. |
| 5,760,399 A | 6/1998 | Trygstad |
| 5,781,289 A | 7/1998 | Sabsabi et al. |
| 5,799,231 A | 8/1998 | Gates et al. |
| 5,831,742 A | 11/1998 | Watson et al. |
| 5,905,571 A | 5/1999 | Butler et al. |
| 5,939,717 A | 8/1999 | Mullins |
| 5,941,821 A | 8/1999 | Chou |
| 5,945,676 A | 8/1999 | Khalil et al. |
| 5,946,088 A | 8/1999 | Aldridge |
| 5,946,089 A | 8/1999 | Duer |
| 5,991,048 A | 11/1999 | Karlson et al. |
| 6,006,585 A | 12/1999 | Forster |
| 6,040,914 A | 3/2000 | Bortz et al. |
| 6,124,937 A | 9/2000 | Mittenzwey et al. |
| 6,137,108 A | 10/2000 | DeThomas et al. |
| 6,176,323 B1 | 1/2001 | Weirich et al. |
| 6,198,531 B1 * | 3/2001 | Myrick et al. ............ 356/300 |
| 6,304,854 B1 | 10/2001 | Harris |
| 6,317,648 B1 | 11/2001 | Sleep et al. |
| 6,347,131 B1 | 2/2002 | Gusterson |
| 6,350,389 B1 | 2/2002 | Fujishima et al. |
| 6,420,708 B2 | 7/2002 | Wilks, Jr. et al. |
| 6,430,513 B1 | 8/2002 | Wang et al. |
| 6,437,326 B1 | 8/2002 | Yamate et al. |
| 6,469,785 B1 | 10/2002 | Duveneck et al. |
| 6,476,384 B1 | 11/2002 | Mullins et al. |
| 6,490,035 B1 | 12/2002 | Folestad et al. |
| 6,517,230 B1 | 2/2003 | Afnan et al. |
| 6,522,945 B2 | 2/2003 | Sleep et al. |
| 6,529,276 B1 | 3/2003 | Myrick |
| 6,573,999 B1 | 6/2003 | Yang |
| 6,600,560 B2 | 7/2003 | Mikkelsen et al. |
| 6,630,663 B2 | 10/2003 | Murphy et al. |
| 6,667,802 B2 | 12/2003 | Faus et al. |
| 6,690,464 B1 | 2/2004 | Lewis et al. |
| 6,697,195 B2 | 2/2004 | Weber et al. |
| 6,707,043 B2 | 3/2004 | Coates et al. |
| 6,711,503 B2 | 3/2004 | Haaland |
| 6,737,654 B2 | 5/2004 | Ducourant |
| 6,741,335 B2 | 5/2004 | Kinrot et al. |
| 6,748,334 B1 | 6/2004 | Perez et al. |
| 6,765,212 B2 | 7/2004 | Goetz et al. |
| 6,771,369 B2 | 8/2004 | Rzasa et al. |
| 6,776,517 B2 | 8/2004 | Afnan et al. |
| 6,798,518 B2 | 9/2004 | DiFoggio et al. |
| 6,853,447 B2 | 2/2005 | Goetz |
| 6,870,629 B1 | 3/2005 | Vogel et al. |
| 6,952,267 B2 | 10/2005 | Rarac |
| 6,980,285 B1 | 12/2005 | Hansen |
| 6,982,431 B2 | 1/2006 | Modlin et al. |
| 6,995,840 B2 | 2/2006 | Hagler |
| 7,006,214 B2 | 2/2006 | Rzasa et al. |
| 7,123,844 B2 | 10/2006 | Myrick |
| 7,138,156 B1 | 11/2006 | Myrick et al. |
| 7,145,145 B2 | 12/2006 | Benson |
| 7,173,239 B2 | 2/2007 | DiFoggio |
| 7,245,374 B2 | 7/2007 | Hendriks |
| 7,271,883 B2 | 9/2007 | Newell et al. |
| 7,399,968 B2 | 7/2008 | Lewis et al. |
| 7,405,825 B2 | 7/2008 | Schuurmans et al. |
| 7,411,729 B2 | 8/2008 | Lyama et al. |
| 7,569,354 B2 | 8/2009 | Okano et al. |
| 7,623,233 B2 | 11/2009 | Freese et al. |
| 7,652,767 B2 | 1/2010 | Harsh et al. |
| 7,671,973 B2 | 3/2010 | Van Beek et al. |
| 7,697,141 B2 | 4/2010 | Jones et al. |
| 7,853,104 B2 | 12/2010 | Oota et al. |
| 7,889,346 B2 | 2/2011 | Myrick et al. |
| 7,911,605 B2 | 3/2011 | Myrick et al. |
| 7,920,258 B2 | 4/2011 | Myrick et al. |
| 2001/0034064 A1 | 10/2001 | Turner et al. |
| 2002/0008215 A1 | 1/2002 | Evans |
| 2002/0050567 A1 | 5/2002 | Boudet et al. |
| 2002/0071118 A1 * | 6/2002 | Shinbori et al. ............ 356/326 |
| 2002/0108892 A1 | 8/2002 | Goetz et al. |
| 2002/0109094 A1 | 8/2002 | Goetz et al. |
| 2002/0154315 A1 | 10/2002 | Myrick |
| 2003/0056581 A1 | 3/2003 | Turner et al. |
| 2003/0059820 A1 | 3/2003 | Vo-Dinh |
| 2003/0071988 A1 | 4/2003 | Smith et al. |
| 2003/0094495 A1 | 5/2003 | Knowles et al. |
| 2003/0111606 A1 | 6/2003 | Berghmans et al. |
| 2003/0117628 A1 | 6/2003 | Harju et al. |
| 2003/0202179 A1 | 10/2003 | Larsen et al. |
| 2004/0012782 A1 | 1/2004 | Mason et al. |
| 2004/0106098 A1 | 6/2004 | Chen et al. |
| 2004/0160601 A1 | 8/2004 | Womble et al. |
| 2004/0227086 A1 | 11/2004 | Haug et al. |
| 2005/0032235 A1 | 2/2005 | Tummala et al. |
| 2005/0077476 A1 | 4/2005 | Poteet et al. |
| 2005/0087132 A1 | 4/2005 | Dickey et al. |
| 2005/0167264 A1 | 8/2005 | Sternbergh et al. |
| 2005/0251289 A1 | 11/2005 | Bonney et al. |
| 2005/0264815 A1 | 12/2005 | Wechsler et al. |
| 2005/0288906 A1 | 12/2005 | Drennen, III et al. |
| 2006/0051036 A1 | 3/2006 | Treado et al. |
| 2006/0093523 A1 | 5/2006 | Norman |
| 2006/0142955 A1 | 6/2006 | Jones et al. |
| 2006/0153492 A1 | 7/2006 | Treves et al. |
| 2006/0158734 A1 | 7/2006 | Schuurmans et al. |
| 2006/0197015 A1 | 9/2006 | Sterling et al. |
| 2006/0276697 A1 | 12/2006 | Demuth et al. |
| 2007/0035737 A1 | 2/2007 | Andrews et al. |
| 2007/0137292 A1 | 6/2007 | Xian et al. |
| 2007/0201136 A1 | 8/2007 | Myrick |
| 2007/0282647 A1 | 12/2007 | Freese et al. |
| 2007/0294094 A1 | 12/2007 | Alessandrini et al. |
| 2008/0111064 A1 | 5/2008 | Andrews et al. |
| 2008/0231849 A1 | 9/2008 | Myrick |
| 2008/0276687 A1 | 11/2008 | Myrick et al. |
| 2008/0309930 A1 | 12/2008 | Rensen |
| 2009/0002697 A1 | 1/2009 | Freese et al. |
| 2009/0015819 A1 | 1/2009 | Van Beek et al. |
| 2009/0033933 A1 | 2/2009 | Myrick |
| 2009/0073433 A1 | 3/2009 | Myrick et al. |
| 2009/0097024 A1 | 4/2009 | Blackburn et al. |
| 2009/0140144 A1 | 6/2009 | Myrick et al. |
| 2009/0216504 A1 | 8/2009 | Priore et al. |
| 2009/0219538 A1 | 9/2009 | Myrick et al. |
| 2009/0219539 A1 | 9/2009 | Myrick et al. |
| 2009/0250613 A1 | 10/2009 | Myrick et al. |
| 2009/0299946 A1 | 12/2009 | Myrick et al. |
| 2009/0316150 A1 | 12/2009 | Myrick et al. |
| 2010/0042348 A1 | 2/2010 | Bakker |
| 2010/0073666 A1 | 3/2010 | Perkins et al. |
| 2010/0141952 A1 | 6/2010 | Myrick et al. |
| 2010/0149537 A1 | 6/2010 | Myrick et al. |
| 2010/0153048 A1 | 6/2010 | Myrick et al. |
| 2010/0182600 A1 | 7/2010 | Freese et al. |
| 2010/0195105 A1 | 8/2010 | Myrick et al. |
| 2010/0211329 A1 | 8/2010 | Farquharson et al. |
| 2010/0245096 A1 | 9/2010 | Jones et al. |
| 2010/0265509 A1 | 10/2010 | Jones et al. |
| 2010/0302539 A1 | 12/2010 | Myrick et al. |
| 2010/0305741 A1 | 12/2010 | Myrick |
| 2010/0328669 A1 | 12/2010 | Myrick et al. |

FOREIGN PATENT DOCUMENTS

| | | | |
|---|---|---|---|
| EP | 1974201 A1 | 10/2008 |
| EP | 2087328 A2 | 8/2009 |
| EP | 2140238 A1 | 1/2010 |
| JP | 57142546 A | 9/1982 |
| WO | 2004057284 A1 | 7/2004 |
| WO | 2005/062006 A1 | 7/2005 |
| WO | 2005062986 A1 | 7/2005 |
| WO | 2006/031733 A2 | 3/2006 |
| WO | 2006/064446 A1 | 6/2006 |
| WO | 2006/137902 A2 | 12/2006 |
| WO | 2007061435 A1 | 5/2007 |
| WO | 2007061436 A1 | 5/2007 |
| WO | 2007061437 A1 | 5/2007 |
| WO | 2007062202 A1 | 5/2007 |
| WO | 2007062224 A1 | 5/2007 |
| WO | 2007064578 A1 | 6/2007 |
| WO | 2008002903 A2 | 1/2008 |
| WO | PCT/US2008/058382 | 3/2008 |
| WO | 2008057912 A2 | 5/2008 |
| WO | 2008057913 A2 | 5/2008 |
| WO | 2008/121684 A1 | 10/2008 |

OTHER PUBLICATIONS

M.L. Myrick et al., "Application of Multivariate Optical Computing to Near-Infrared Imaging", Vibration Spectroscopy-based Sensor System, Proceedings of SPIE, vol. 4577, pp. 148-157, 2002.

E.B. Martin et al., "Process Performance Monitoring Using Multivariate Statistical Process Control", IEE Proc.—Control Theory Appl., vol. 143, No. 2, pp. 132-144, Mar. 1996.

Mandelis et al., "Theory of Photopyroelectric Spectroscopy of Solids", Journal of Applied Physics, vol. 57, No. 9, pp. 4421-4430, 1985.

Zagonel et al., "Multivariate Monitoring of Soybean Oil Ethanolysis by FTIR", Talanta, vol. 63, No. 4, pp. 1021-1025, 2004.

Inon et al., "Combination of Mid- and Near-Infrared Spectroscopy for the Determination of the Quality Properties of Beers", Analytica Chimica Acta, vol. 571, No. 2, pp. 167-174, 2006.

Czarnik-Matusewicz et al., Temperature-Dependent Water Structural Transitions Examined by Near-IR and Mid-IR Spectra Analyzed by Multivariate Curve Resolution and Two-Dimensional Correlation Spectroscopy', Analytica Chimica Acta, vol. 544, No. 1-2, pp. 15-25, 2005.

Pimentel et al., "Determination of Biodiesel Content when Blended with Mineral Diesel Fuel Using Infrared Spectroscopy and Multivariate Calibration", Microchemical Journal, vol. 82, No. 2, pp. 201-206, 2006.

Ghesti et al., "Application of Raman Spectroscopy to Monitor and Quantify Ethyl Esters in Soybean Oil Transesterification", Journal of the American Oil Chemists' Society, vol. 83, pp. 597-601, 2006.

Dereniak et al., *Infrared Detectors and Systems*, John Wiley & Sons: New York, Chapter 9, pp. 395-438, 1996.

Prystay et al., "Thermophysical Measurements and Interfacial Adhesion Studies in Ultrathin Polymer Films Using Homodyne Photothermal Spectrometry", Applied Spectroscopy, vol. 47, No. 4, pp. 501-514, 1993.

Simcock et al, "Tuning D* with Modified Thermal Detectors", Applied Spectroscopy, vol. 60, No. 12, pp. 1469-1476, 2006.

Lang, "Ferroelectric Polymers and Ceramic-Polymer Composites", Key Engineering Materials, vol. 92-93, pp. 83-142, 1994.

Profeta et al., "Spectral Resolution in Multivariate Optical Computing", Spectrochimica Acta Part A: Molecular and Biomolecular Spectroscopy, vol. 67, pp. 483-502, 2007.

Power et al., "Rapid Recovery of Wide Bandwidth Photothermal Signals via Homodyne Photothermal Spectrometry: Theory and Methodology", Applied Spectroscopy, vol. 47, No. 4, pp. 489-500, 1993.

Workman, Handbook of Organic Compounds: NIR, IR, Raman and UV-Vis Spectra Featuring Polymers and Surfactants (a 3-volume set); Academic Press: San Diego, vol. 3, pp. 96-160, 2001.

Knothe, "Analyzing Biodiesel: Standards and Other Methods", Journal of the American Oil Chemists Society, vol. 83, No. 10, pp. 823-833, 2006.

E.D. Palik, *Handbook of Optical Constants of Solids I*, Academic Press, San Diego, pp. 350-357, 1998.

M.L. Myrick, "Multivariate optical elements simplify spectroscopy", Laser Focus World 38, 91-94, 2002.

O. Soyemi et al., "Design and testing of a multivariate optical element: The first demonstration of multivariate optical computing for predictive spectroscopy", Anal. Chem. 73, No. 6, pp. 1069-1079, (2001).

M.L. Myrick et al., "A single-element all-optical approach to chemometric prediction", Vib. Spectrosc. 28, 73-81, 2002.

A.M.C. Prakash et al., "Optical regression: a method for improving quantitative precision of multivariate prediction with single channel spectrometers", Chemom. Intell. Lab. Syst. 46, 265-274, 1999.

R.A. Deverse et al., "Realization of the Hadamard multiplex advantage using a programmable optical mask in a dispersive flat-field near-infrared spectrometer", Appl. Spectrosc. 54, 1751-1758, 2000.

F.G. Haibach et al., "Precision in multivariate optical computing", Appl. Optics 43, 2130-2140, 2004.

M.L. Myrick et al., "Application of multivariate optical computing to simple near-infrared point measurements", Proceedings of the SPIE, Bellingham, VA, US, vol. 4574, pp. 208-215, 2002.

O.S. Heavens, *Optical Properties of Thin Solid Films*, Dover Publications, Inc., Mineola, USA, pp. 62-81, 242-249, 1991.

S. Betancourt et al., "Analyzing Hydrocarbons in the Borehole", Oilfield Review, pp. 54-61, Autumn 2003.

D. Eastwood et al., "Field applications of stand-off sensing using visible/NIR multivariate optical computing", Ground and Air Pollution Monitoring and Remediation, SPIE vol. 4199, pp. 105-114, 2001.

Haibach et al., "On-line Reoptimization of Filter Designs for Multivariate Optical Elements", Applied Optics, vol. 42, No. 10, pp. 1833-1838, Apr. 1, 2003.

Mullins et al., "Gas-Oil Ratio of Live Crude Oils Determined by Near-Infrared Spectroscopy", Optical Methods for Industrial Processes, Proceedings of SPIE vol. 4201, pp. 73-81, 2001.

M.P. Nelson et al., "Multivariate optical computation for predictive spectroscopy", SPIE Vo. 3261, pp. 232-243, 1998.

O. Soyemi et al., "A Simple Optical Computing Device for Chemical Analysis", Proceedings of SPIE Vo. 4284, pp. 17-28, 2001.

O. Soyemi et al., "Design of angle tolerant multivariate optical elements for chemical imaging", Applied Optics, vol. 41, No, 10, pp. 1936-1941, Apr. 1, 2002.

O. Soyemi et al., "Nonlinear Optimization Algorithm for Multivariate Optical Element Design", Applied Spectroscopy, vol. 56, No. 4, pp. 477-487, 2002.

O. Soyemi et al., "Novel Filter Design Algorithm for Multivariate Optical Computing", Advanced Environmental and Chemical Sensing Technology, Proceedings of SPIE Vo. 4205, pp. 288-299, 2001.

Strausz et al., "About the Colloidal Nature of Asphaltenes and the MW of Covalent Monomeric Units", American Chemical Society, Energy and Fuels 16, No. 4, pp. 809-822, 2002 (abstract).

N. Aske et al., "Determination of Saturate, Aromatic, Resin, and Asphitenic (SARA) Components in Crude Oils by Means of Infrared and Near-Infrared Spectroscopy", American Chemical Society, Energy and Fuels 15, No. 5, pp. 1304-1312, 2001.

N. Aske et al., "Asphaltene Aggregation from Crude Oils and Models Systems Studied by High-Pressure NIR Spectroscopy", Energy and Fuels, American Chemical Society, 16, No. 5, pp. 1287-1295, 2002.

Sastry et al., "Determination of Physiocochemical Properties and Carbon-Type Analysis of Base Oils Using Mid-IR Spectroscopy and Partial Least Squares Regression Analysis", American Chemical Society, Energy and Fuels 12, No. 2, pp. 304-311, 1998.

Y. Yan et al. "Fluorescence Fingerprint of Waters: Excitation-Emission Matrix Spectroscopy as a Tracking Tool", Applied Spectroscopy, vol. 54, No. 10, pp. 1539-1542, 2000.

M.P. Nelson et al., "Multivariate optical computation for predictive spectroscopy", Analytical Chemistry, vol. 70, No. 1, pp. 73-82, Jan. 1, 1998.

M.P. Nelson et al., "Fabrication and evaluation of a dimension-reduction fiberoptic system for chemical imaging applications", Review of Scientific Instruments, vol. 70, No. 6, pp. 2836-2843, Jun. 1999.

M.L. Myrick, "New approaches to implementing predictive spectroscopy", Proceedings of the SPIE Conference on Pattern Recognition, Chemometrics, and Imaging for Optical Environmental Monitoring, SPIE vol. 3854, pp. 98-102, Sep. 1999.

M. Groner et al., "Identification of Major Water-Soluble Fluorescent Components of Some Petrochemicals", Marine Pollution Bulletin, vol. 42, No. 10, pp. 935-941, 2001.

M.V. Schiza et al., "Use of a 2D to 1D Dimension Reduction Fiber-Optic Array for Multiwavelength Imaging Sensors", Applied Spectroscopy, vol. 55, No. 2, pp. 217-226, 2001.

M.L. Myrick et al., "Spectral tolerance determination for multivariate optical element design", Fresenius J Anal Chem, 369:351-355, 2001.

R.J. Priore et al., "Miniature Stereo Spectral Imaging System for Multivariate Optical Computing", Applied Spectroscopy, vol. 58, No. 7, pp. 870-873, 2004.

M.L. Myrick et al., "Use of Molecular Symmetry to Describe Pauli Principle Effects on the Vibration-Rotation Spectroscopy of $CO_2(g)$", Journal of Chemical Education, vol. 81, No. 3, pp. 379-382, Mar. 2004.

M.N. Simcock et al., "Precision in imaging multivariate optical computing", Applied Optics, vol. 46., No. 7, pp. 1066-1080, Mar. 1, 2007.

Ozturk et al., "Filtering Characteristics of Hybrid Integrated Polymer and Compound Semiconductor Waveguides", In: Journal of Lightwave Technology, vol. 20, No. 8, pp. 1530-1536, Aug. 2002.

P.G. Miney et al., "A New Optically Reflective Thin Layer Electrode (ORTLE) Window: Gold on a Thin Porous Alumina Film Used to Observe the Onset of Water Reduction", Electroanalysis, 16, No. 1-2, pp. 113-119, 2004.

Mullins et al., "Gas-Oil Ratio of Live Crude Oils Determined by Near-Infrared Spectroscopy", Applied Spectroscopy, vol. 55, No. 2, pp. 197-201, 2001.

\* cited by examiner

OPTICAL ANALYSIS SYSTEM AND METHOD FOR REAL TIME MULTIVARIATE OPTICAL COMPUTING

CROSS-REFERENCE TO RELATED APPLICATIONS

This application claims priority to PCT Patent Application Serial Number PCT/US2006/045357, filed Nov. 27, 2006, which claims benefit of U.S. Provisional Patent Application Ser. No. 60/740,078, filed Nov. 28, 2005, all of which are incorporated herein by reference in their entireties.

BACKGROUND OF THE DISCLOSURE

Light conveys information through data. When light interacts with matter, for example, it carries away information about the physical and chemical properties of the matter. A property of the light, for example, its intensity, may be measured and interpreted to provide information about the matter with which it interacted. That is, the data carried by the light through its intensity may be measured to derive information about the matter. Similarly, in optical communications systems, light data is manipulated to convey information over an optical transmission medium, for example fiber optic cable. The data is measured when the light signal is received to derive information.

In general, a simple measurement of light intensity is difficult to convert to information because it likely contains interfering data. That is, several factors may contribute to the intensity of light, even in a relatively restricted wavelength range. It is often impossible to adequately measure the data relating to one of these factors since the contribution of the other factors is unknown.

It is possible, however, to derive information from light. An estimate may be obtained, for example, by separating light from several samples into wavelength bands and performing a multiple linear regression of the intensity of these bands against the results of conventional measurements of the desired information for each sample. For example, a polymer sample may be illuminated so that light from the polymer carries information such as the sample's ethylene content. Light from each of several samples may be directed to a series of bandpass filters which separate predetermined wavelength bands from the light. Light detectors following the bandpass filters measure the intensity of each light band. If the ethylene content of each polymer sample is measured using conventional means, a multiple linear regression of ten measured bandpass intensities against the measured ethylene content for each sample may produce an equation such as:

$$y = a_0 + a_1 w_1 + a_2 w_2 + \ldots + a_{10} w_{10} \quad \text{(``Equation 1'')}$$

where y is ethylene content, $a_n$ are constants determined by the regression analysis, and $w_n$ is light intensity for each wavelength band.

Equation 1 may be used to estimate ethylene content of subsequent samples of the same polymer type. Depending on the circumstances, however, the estimate may be unacceptably inaccurate since factors other than ethylene may affect the intensity of the wavelength bands. These other factors may not change from one sample to the next in a manner consistent with ethylene.

A more accurate estimate may be obtained by compressing the data carried by the light into principal components. To obtain the principal components, spectroscopic data is collected for a variety of samples of the same type of light, for example from illuminated samples of the same type of polymer. For example, the light samples may be spread into their wavelength spectra by a spectrograph so that the magnitude of each light sample at each wavelength may be measured. This data is then pooled and subjected to a linear-algebraic process known as singular value decomposition (SVD). SVD is at the heart of principal component analysis, which should be well understood in this art. Briefly, principal component analysis is a dimension reduction technique, which takes m spectra with n independent variables and constructs a new set of eigenvectors that are linear combinations of the original variables. The eigenvectors may be considered a new set of plotting axes. The primary axis, termed the first principal component, is the vector, which describes most of the data variability. Subsequent principal components describe successively less sample variability, until only noise is described by the higher order principal components.

Typically, the principal components are determined as normalized vectors. Thus, each component of a light sample may be expressed as $x_n z_n$, where $x_n$ is a scalar multiplier and $z_n$ is the normalized component vector for the $n_{th}$ component. That is, $z_n$ is a vector in a multi-dimensional space where each wavelength is a dimension. As should be well understood, normalization determines values for a component at each wavelength so that the component maintains it shape and so that the length of the principal component vector is equal to one. Thus, each normalized component vector has a shape and a magnitude so that the components may be used as the basic building blocks of all light samples having those principal components. Accordingly, each light sample may be described in the following format by the combination of the normalized principal components multiplied by the appropriate scalar multipliers:

$$x_1 z_1 + x_2 z_2 + \ldots + x_n z_n.$$

The scalar multipliers $x_n$ may be considered the "magnitudes" of the principal components in a given light sample when the principal components are understood to have a standardized magnitude as provided by normalization.

Because the principal components are orthogonal, they may be used in a relatively straightforward mathematical procedure to decompose a light sample into the component magnitudes, which accurately describe the data in the original sample. Since the original light sample may also be considered a vector in the multi-dimensional wavelength space, the dot product of the original signal vector with a principal component vector is the magnitude of the original signal in the direction of the normalized component vector. That is, it is the magnitude of the normalized principal component present in the original signal. This is analogous to breaking a vector in a three dimensional Cartesian space into its X, Y and Z components. The dot product of the three-dimensional vector with each axis vector, assuming each axis vector has a magnitude of 1, gives the magnitude of the three dimensional vector in each of the three directions. The dot product of the original signal and some other vector that is not perpendicular to the other three dimensions provides redundant data, since this magnitude is already contributed by two or more of the orthogonal axes.

Because the principal components are orthogonal, or perpendicular, to each other, the dot, or direct, product of any principal component with any other principal component is zero. Physically, this means that the components do not interfere with each other. If data is altered to change the magnitude of one component in the original light signal, the other components remain unchanged. In the analogous Cartesian example, reduction of the X component of the three dimensional vector does not affect the magnitudes of the Y and Z components.

Principal component analysis provides the fewest orthogonal components that can accurately describe the data carried by the light samples. Thus, in a mathematical sense, the principal components are components of the original light that do not interfere with each other and that represent the most compact description of the entire data carried by the light. Physically, each principal component is a light signal that forms a part of the original light signal. Each has a shape over some wavelength range within the original wavelength range. Summing the principal components produces the original signal, provided each component has the proper magnitude.

The principal components comprise a compression of the data carried by the total light signal. In a physical sense, the shape and wavelength range of the principal components describe what data is in the total light signal while the magnitude of each component describes how much of that data is there. If several light samples contain the same types of data, but in differing amounts, then a single set of principal components may be used to exactly describe (except for noise) each light sample by applying appropriate magnitudes to the components.

The principal components may be used to accurately estimate information carried by the light. For example, suppose samples of a certain brand of gasoline, when illuminated, produce light having the same principal components. Spreading each light sample with a spectrograph may produce wavelength spectra having shapes that vary from one gasoline sample to another. The differences may be due to any of several factors, for example differences in octane rating or lead content.

The differences in the sample spectra may be described as differences in the magnitudes of the principal components. For example, the gasoline samples might have four principal components. The magnitudes $x_n$ of these components in one sample might be J, K, L, and M, whereas in the next sample the magnitudes may be 0.94 J, 1.07K, 1.13 L and 0.86 M. As noted above, once the principal components are determined, these magnitudes exactly describe their respective light samples.

Refineries desiring to periodically measure octane rating in their product may derive the octane information from the component magnitudes. Octane rating may be dependent upon data in more than one of the components. Octane rating may also be determined through conventional chemical analysis. Thus, if the component magnitudes and octane rating for each of several gasoline samples are measured, a multiple linear regression analysis may be performed for the component magnitudes against octane rating to provide an equation such as:

$$y=a_0+a_1x_1+a_2x_2+a_3x_3+a_4x_4 \quad \text{(``Equation 2'')}$$

where y is octane rating, $a_n$ are constants determined by the regression analysis, and $x_1$, $x_2$, $x_3$ and $x_4$ are the first, second, third and fourth principal component magnitudes, respectively.

Using Equation 2, which may be referred to as a regression vector, refineries may accurately estimate octane rating of subsequent gasoline samples. Conventional systems perform regression vector calculations by computer, based on spectrograph measurements of the light sample by wavelength. The spectrograph system spreads the light sample into its spectrum and measures the intensity of the light at each wavelength over the spectrum wavelength range. If the regression vector in the Equation 2 form is used, the computer reads the intensity data and decomposes the light sample into the principal component magnitudes $x_n$ by determining the dot product of the total signal with each component. The component magnitudes are then applied to the regression equation to determine octane rating.

To simplify the procedure, however, the regression vector is typically converted to a form that is a function of wavelength so that only one dot product is performed. Each normalized principal component vector $z_n$ has a value over all or part of the total wavelength range. If each wavelength value of each component vector is multiplied by the regression constant $a_n$ corresponding to the component vector, and if the resulting weighted principal components are summed by wavelength, the regression vector takes the following form:

$$y=a_0+b_1u_1+b_2u_2+\ldots+b_nu_n \quad \text{(``Equation 3'')}$$

where y is octane rating, $a_0$ is the first regression constant from Equation 2, $b_n$ is the sum of the multiple of each regression constant $a_n$ from Equation 2 and the value of its respective normalized regression vector at wavelength n, and $u_n$ is the intensity of the light sample at wavelength n. Thus, the new constants define a vector in wavelength space that directly describes octane rating. The regression vector in a form as in Equation 3 represents the dot product of a light sample with this vector.

Normalization of the principal components provides the components with an arbitrary value for use during the regression analysis. Accordingly, it is very unlikely that the dot product result produced by the regression vector will be equal to the actual octane rating. The number will, however, be proportional to the octane rating. The proportionality factor may be determined by measuring octane rating of one or more samples by conventional means and comparing the result to the number produced by the regression vector. Thereafter, the computer can simply scale the dot product of the regression vector and spectrum to produce a number approximately equal to the octane rating.

In a conventional spectroscopy analysis system, a laser directs light to a sample by a bandpass filter, a beam splitter, a lens and a fiber optic cable. Light is reflected back through the cable and the beam splitter to another lens to a spectrograph. The spectrograph separates light from the illuminated sample by wavelength so that a detection device such as a charge couple detector can measure the intensity of the light at each wavelength. The charge couple detector is controlled by controller and cooled by a cooler. The detection device measures the light intensity of light from the spectrograph at each wavelength and outputs this data digitally to a computer, which stores the light intensity over the wavelength range. The computer also stores a previously derived regression vector for the desired sample property, for example octane, and sums the multiple of the light intensity and the regression vector intensity at each wavelength over the sampled wavelength range, thereby obtaining the dot product of the light from the substance and the regression vector. Since this number is proportional to octane rating, the octane rating of the sample is identified.

Since the spectrograph separates the sample light into its wavelengths, a detector is needed that can detect and distinguish the relatively small amounts of light at each wavelength. Charge couple devices provide high sensitivity throughout the visible spectral region and into the near infrared with extremely low noise. These devices also provide high quantum efficiency, long lifetime, imaging capability and solid-state characteristics. Unfortunately, however, charge couple devices and their required operational instrumentation are very expensive. Furthermore, the devices are sensitive to environmental conditions. In a refinery, for example, they must be protected from explosion, vibration and temperature fluctuations and are often placed in protective housings approximately the size of a refrigerator. The power requirements, cooling requirements, cost, complexity and maintenance requirements of these systems have made them impractical in many applications.

Multivariate optical computing (MOC) is a powerful predictive spectroscopic technique that incorporates a multi-wavelength spectral weighting directly into analytical instrumentation. This is in contrast to traditional data collection routines where digitized spectral data is post processed with a computer to correlate spectral signal with analyte concentration. Previous work has focused on performing such spectral weightings by employing interference filters called Multivariate Optical Elements (MOEs). Other researchers have realized comparable results by controlling the staring or integration time for each wavelength during the data collection process. All-optical computing methods have been shown to produce similar multivariate calibration models, but the measurement precision via an optical computation is superior to a traditional digital regression.

MOC has been demonstrated to simplify the instrumentation and data analysis requirements of a traditional multivariate calibration. Specifically, the MOE utilizes a thin film interference filter to sense the magnitude of a spectral pattern. A no-moving parts spectrometer highly selective to a particular analyte may be constructed by designing simple calculations based on the filter transmission and reflection spectra. Other research groups have also performed optical computations through the use of weighted integration intervals and acousto-optical tunable filters, digital mirror arrays and holographic gratings.

The measurement precision of digital regression has been compared to various optical computing techniques including MOEs, positive/negative interference filters and weighted-integration scanning optical computing. In a high signal condition where the noise of the instrument is limited by photon counting, optical computing offers a higher measurement precision when compared to its digital regression counterpart. The enhancement in measurement precision for scanning instruments is related to the fraction of the total experiment time spent on the most important wavelengths. While the detector integrates or coadds measurements at these important wavelengths, the signal increases linearly while the noise increases as a square root of the signal. Another contribution to this measurement precision enhancement is a combination of the Felgott's and Jacquinot's advantage, which is possessed by MOE optical computing.

The industry requires a system in which the spectral range of the illumination source can be controlled; in which light can be shined directly onto a sample with or without fiber optic probes; and in which the reflected or transmitted light can be analyzed in real time.

SUMMARY OF THE DISCLOSURE

The present disclosure is directed generally to an optical system for multivariate optical computing in real-time. Multivariate optical computing (MOC) is generally described in U.S. Pat. No. 6,198,531 B1 to Myrick et al. and in U.S. Pat. No. 6,529,276 B1 to Myrick as a predictive spectroscopy technique that incorporates a multi-wavelength spectral weighting directly into analytical instrumentation. Both of these patents are incorporated herein for all purposes by reference thereto.

Since multivariate optical element (MOE)-based MOC uses detectors that see all wavelengths emanating from an illumination source simultaneously—including wavelengths that carry no information—measurement noise is reduced and measurement precision is increased in the system of the present subject matter by making the system sensitive primarily to wavelengths carrying information. Additionally, the present subject matter controls a spectral range of the illumination source by using bandpass filters or spectral elements having predetermined transmission characteristics. Further, in some aspects of the present subject matter, the system shines a light signal directly onto a sample and eliminates the use of, for instance, of a fiber optic probe; therefore, the component parts of the exemplary embodiments of the present disclosure are simple and economical to manufacture, assemble and use, with improved signal when the attenuation typical of a fiber optic probe is removed. These and other aspects and advantages of the present disclosure will be apparent from the following description and the attached drawings, or can be learned through practice of the present subject matter.

According to one embodiment of the disclosure, an optical analysis system generally includes an illumination source for shining light or other radiative energy through a set of lenses. Light levels are maximized through the optical system to enhance transmission (reduce loss) of the light. The illumination source subsequently shines the light through a multi-window (e.g.,10-window) chopper wheel. The chopper wheel rotates, for instance, at 40 Hertz (Hz), which produces a light beam modulated at 400 Hz. A modulated light signal is beneficial for reliable performance of the photodetectors in the system. The light beam passes through one or more spectral elements or filters, which control the spectral region of the light, which passes through them (and onto a sample). The light is reflected by a turning mirror down the center of the sampling tube and focused by a lens on the sample. Light is reflected back by the sample through the lens and back down the sampling tube, past the turning mirror. The light passes through a beam splitter with reflects part of the light ("signal A") through a multivariate optical element (MOE) and lens and onto a photodetector. Another part of the light ("signal B") passes through a lens onto another photodetector and acts as a reference signal. The system measures signal A and signal B, and a ratio of the two signals can be used to measure a concentration of the sample, e.g., a chemical of interest. Additionally, monitoring of signal A and/or signal B independently, or in some combination, can provide other information, such as powder segregation, packing of materials, effect of particle size. More specifically, any algebraic combination of signals A and B can be used according to the disclosure; e.g., A and/or B independently; A divided by B; A plus B; A minus B; B divided by A; B minus A, etcetera. For example, a ratio of signal A to signal B can provide a chemical measurement; individually, A signal and/or B signal can provide other homogeneity measures including physical make-up of the sample, packing, particle size, and/or separate physical and chemical properties.

According to another aspect of the disclosure, a method of determining information carried by light includes the steps of providing an optical analysis system having a multivariate optical element disposed to receive a source light from an illumination source; filtering the source light through a spectral element in the optical element analysis system; reflecting the filtered light through an inner region of a cavity in a first direction of a sample to be measured, the cavity defining a second region disposed about the inner region; focusing the reflected light proximate the sample; reflecting the focused light from the sample through the second region in a second direction of a beamsplitter, the light being reflected from the sample carrying data from the sample; splitting the sample carrying light with the beamsplitter into a first light and a second light; optically filtering the data of the first light with the multivariate optical element into an orthogonal component; directing the first light filtered by the multivariate optical element onto a first photodetector; directing the second light onto a second photodetector; and comparing the orthogonal component to information present in the second light to determine a property of the sample. In this aspect, the light is focused on, in or near the sample, the light having a focal point proximate the sample. Also in this aspect, the beamsplifter is a 50/50 beamsplitter.

The method in this aspect may also include the step of modulating the light from about 50 Hz to about 5000 Hz before filtering the light through the spectral element. A further step may include controlling a spectral range of the light source, the spectral element having a predetermined transmission characteristic for controlling the spectral range. Also in this aspect, the spectral element can be two or more spectral elements for controlling the spectral range of the light source.

Further, in this aspect of the disclosure, the method may include measuring a concentration of the sample ratio using a ratio of the first light and the second light. Additional steps may include monitoring the first light, the second light or combinations thereof to assess particle segregation of the sample; monitoring the first light, the second light or combinations thereof to assess density of the sample; monitoring the first light, the second light or combinations thereof to assess affect of particle size in the sample, monitoring the first light, the second light or combinations thereof to measure a chemical in the sample; monitoring the first light, the second light or combinations thereof to measure homogeneity of the sample and combinations of the foregoing steps.

Also in this aspect, the method can include the step of using a fiber optic probe. Moreover, the method may include preparing a chemometric model to make a similar measurement of the light reflected from the sample as a measurement made by the optical analysis system.

Another step may be using the illumination light from the outer annular region with the filtered light through the inner region of the cavity to determine the property of the sample.

In yet another aspect of the disclosure, an optical analysis system can be configured in a transmission mode rather than a reflectance mode as in the foregoing embodiments. In the transmission mode, light would pass through a sample (e.g., a fluid sample) and be collected on a far side of the sample to enable, for instance, study of particle density in the fluid sample in conjunction with a chemical content. More particularly, in this aspect the optical analysis system can be configured to operate in the transmission mode in which the light is shone through the sample to a similar detection system. Additionally, or alternatively, a mirrored surface can be placed within the transmissive sample to reflect the light back into the detection system as described above.

In another aspect of the disclosure, a method of determining information carried by light can include the steps of determining a plurality of orthogonal components of a first portion of a light signal, wherein each of the components has a predetermined shape with respect to a property of the first portion of the light signal that varies over a predetermined wavelength range; determining respective weightings for the orthogonal components so that the magnitude of the orthogonal components in the first portion of the light signal, weighted by the weightings, is proportional to the information present in the first portion in a predetermined relationship; providing an optical filter mechanism configured to optically filter the orthogonal components; disposing the optical filter mechanism to receive the first portion of the light signal; disposing a detector to receive a second portion of the light signal; detecting the property of the first portion of the light signal filtered by the optical filter mechanism; and analyzing the sample in real time by comparing the property of the first portion of the light signal to information in the second portion of the light signal.

In a further aspect of the disclosure, an optical analysis system includes a light source being configured to radiate a first light along a first ray path; a modulator disposed in the first ray path, the modulator being configured to modulate the first light to a desired frequency; a spectral element disposed proximate the modulator, the spectral element being configured to filter the first light for a spectral range of interest of a sample; a cavity in communication with the spectral element, the cavity being configured to direct the first light in a direction of the sample, the sample reflecting the first light as a second light, the cavity being further configured to direct the second light; a beamsplitter being configured to split the second light into a first beam and a second beam; an optical filter mechanism disposed to receive the first beam, the optical filter mechanism being configured to optically filter data carried by the first beam into at least one orthogonal component of the first beam; a first detector mechanism in communication with the optical filter mechanism to measure a property of the orthogonal component to measure the data; and a second detector mechanism being configured to receive the second beam for comparison of the property of the orthogonal component to the second beam.

In this aspect, the cavity includes a first region and a second region, the first region being configured to direct the second light in a direction of the beamsplitter, the second region being configured to direct the first light in a direction of the sample. Also in this aspect, the optical filter mechanism is a multivariate optical element.

Further in this aspect of the disclosure, the optical analysis system can include a gain mechanism in communication with at least one of the optical filter mechanism, the first detector mechanism and the second detector mechanism, the gain mechanism being configured to weight a magnitude of the property of the light orthogonal component. The optical analysis system can also include a mirror disposed proximate the cavity, the mirror being to direct the first light in the cavity in the direction of the sample. Furthermore, the optical analysis system can include a tube disposed about the mirror, the tube being configured to separate the first light from the second light.

In another aspect, an optical analysis system includes an optical filter mechanism disposed to receive a light from a light source and configured to optically filter data carried by the light into at least one orthogonal component of the light; a detector mechanism in operative communication with the optical filter mechanism to measure a property of the at least one orthogonal component to measure the data; and a spectrograph device disposed relative to the light source and the filter mechanism such that the spectrograph device directs the light from the light source to the filter mechanism, the spectrograph device being configured to separate the light into a spectrum.

Additional objects and advantages of the present subject matter are set forth in, or will be apparent to, those of ordinary skill in the art from the detailed description herein. Also, it should be further appreciated that modifications and variations to the specifically illustrated, referred and discussed features and elements hereof may be practiced in various embodiments and uses of the disclosure without departing from the spirit and scope of the subject matter. Variations may include, but are not limited to, substitution of equivalent means, features, or steps for those illustrated, referenced, or discussed, and the functional, operational, or positional reversal of various parts, features, steps, or the like.

Still further, it is to be understood that different embodiments, as well as different presently preferred embodiments, of the present subject matter may include various combinations or configurations of presently disclosed features, steps, or elements, or their equivalents (including combinations of features, parts, or steps or configurations thereof not expressly shown in the figures or stated in the detailed description of such figures). Additional embodiments of the present subject matter, not necessarily expressed in the summarized section, may include and incorporate various combinations of aspects of features, components, or steps referenced in the summarized objects above, and/or other features, components, or steps as otherwise discussed in this application. Those of ordinary skill in the art will better appreciate the features and aspects of such embodiments, and others, upon review of the remainder of the specification.

BRIEF DESCRIPTION OF THE DRAWINGS

A full and enabling disclosure of the present subject matter, including the best mode thereof, directed to one of ordinary skill in the art, is set forth in the specification, which makes reference to the appended figures, in which.

DETAILED DESCRIPTION OF THE DISCLOSURE

Figure 1:
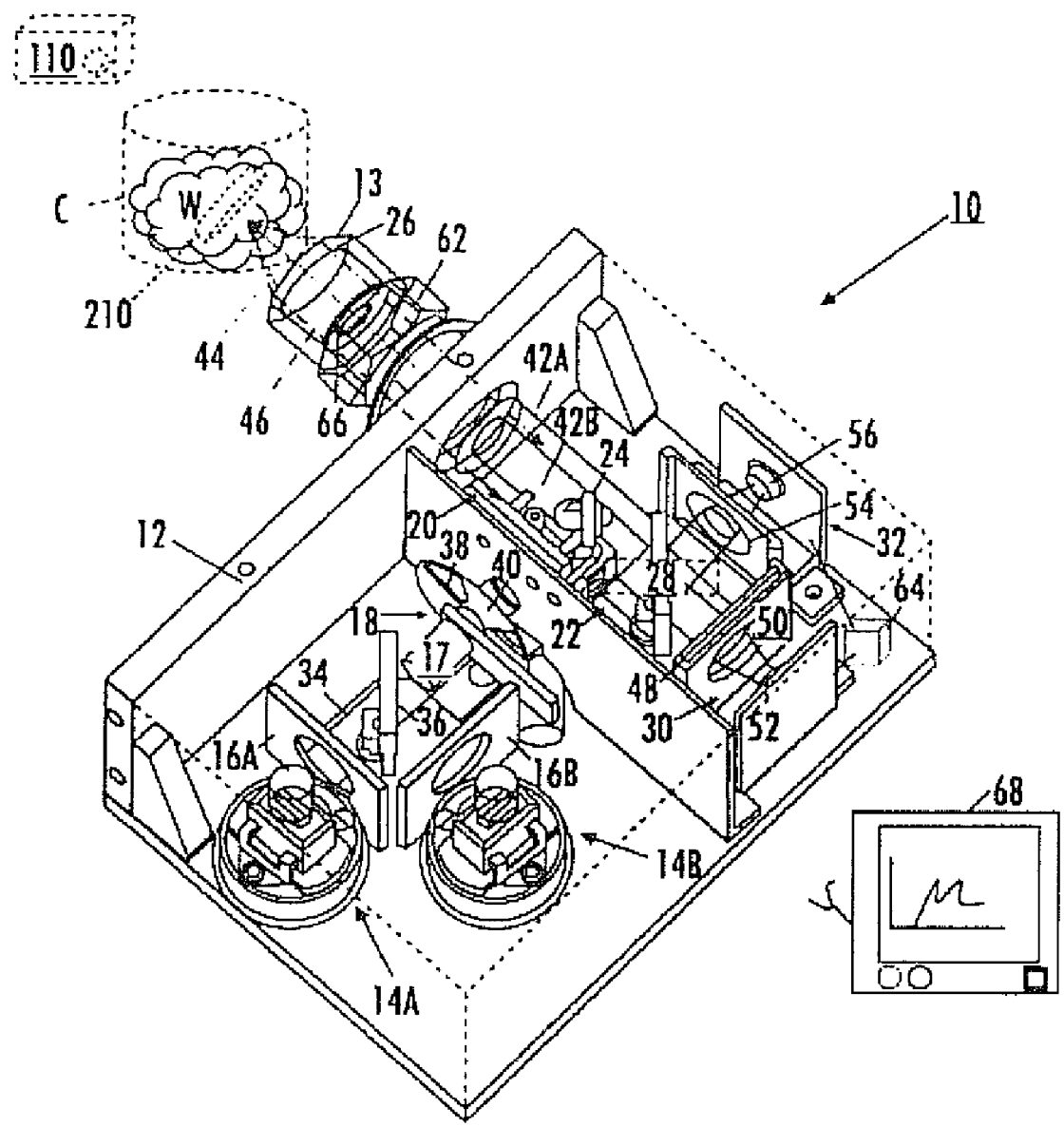
FIG. 1 is a top perspective view of one embodiment of a real time analyte measurement system according to an aspect of the present disclosure.

Detailed reference will now be made to the drawings in which examples embodying the present subject matter are shown. The detailed description uses numerical and letter designations to refer to features of the drawings. Like or similar designations of the drawings and description have been used to refer to like or similar parts of various exemplary embodiments.

The drawings and detailed description provide a full and written description of the present subject matter, and of the manner and process of making and using various exemplary embodiments, so as to enable one skilled in the pertinent art to make and use them, as well as the best mode of carrying out the exemplary embodiments. However, the examples set forth in the drawings and detailed description are provided by way of explanation only and are not meant as limitations of the disclosure. The present subject matter thus includes any modifications and variations of the following examples as come within the scope of the appended claims and their equivalents.

Definitions

Within the context of the present description, the following terms may have the following meanings:

As used herein, the term "sample" may mean an analyte undergoing analysis over a range of conditions. The sample can be a solid or a fluid including but not limited to a powder, a pharmaceutical powder mixed with lactose and other excipient materials, a chemical, a polymer, a petroleum product, a solution, a dispersion, an emulsion and combinations of these solids and fluids.

As used herein, the term "fluid" may mean a continuous amorphous substance including a liquid or a gas that tends to flow and to conform to an outline of its container.

As used herein, the term "light" may mean any form of radiation or radiative energy including, for instance, visible light or light in the infrared region. "Light" is also referred to herein as a light signal, a light beam, a light ray and the like to mean any form of radiative energy in the electromagnetic spectrum.

As used herein, the term "transmission" may mean transmission of radiative energy onto a surface of a sample; penetration, however slight, into a sample such as a particulate sample or opaque fluid sample; or passage through a sample such as a fluid sample.

As used herein, the term "spectral element" may mean one or more spectral elements, including one or more multivariate optical elements, arranged in proximity to each other, or combined together, in a multivariate optical analysis system. In one aspect, the term "spectral element" may mean a composite multivariate optical analysis system.

As used herein, the term "proximate" may mean adjacent, onto, into, within, or the like.

It is to be understood by one of ordinary skill in the art that the following discussion simply describes exemplary embodiments and is not intended as limiting the broader aspects of the present disclosure.

Discussion

As generally shown in the figures, an optical analysis system according to an aspect of the disclosure is designated by the element number 10. In this embodiment, the optical analysis system 10 broadly includes a housing 12, a plurality of illumination or light sources 14A, 14B, a concentric light tube or cavity 22, a focusing lens 26, at least one beam splitter 28, a first detector 30 including a multivariate optical element 48 and a second detector 32. Although the figures, which are about to be described in detail, show a square- or rectangle-shaped, metallic housing 12 and two detectors 30, 32 arranged therein, the skilled artisan will instantly appreciate that a variety of shapes, dimensions, component placements and material makeup of the components can be substituted for the examples shown according to various requirements such as government regulations, customer specifications and the like.

Moreover, as discussed below with respect to another embodiment of the disclosure, a workpiece or sample W can be analyzed using a PCR-type model without the beamsplifter 28 in an off-line approach. The skilled artisan will also understand that although the system can be a measurement system operating in reflectance mode, the system can also be configured to operate in a transmission mode in which light is shone through the sample W from an incident side of the sample W to a similar detection system 110 on another side of the sample W. Alternatively, or additionally, a mirrored surface 210 can be placed within the transmissive sample to reflect the light back into the detection system 10. Therefore, the disclosure is not limited only to the examples shown in the figures.

With particular reference to FIG. 1, the housing 12 (shown partially in phantom for clarity) can be metal such as stainless steel, a plastic material such as high-density polyethylene (HDPE) or any durable material for protecting the components of the optical analysis system 10. As shown, sampling of the sample W is accomplished through a window 13 in the enclosed optical analysis system 10. Accordingly, the enclosed optical analysis system 10 can be used in a dangerous (e.g., explosive) environment. As will be described in detail below, the window 13 is transmissive in a known manner in a spectral region of interest.

As briefly introduced above, the illumination sources 14A, 14B are chosen to provide a source light 34, which has a spectral range determined by a spectral range of interest for the intended sample measurement. The illumination sources 14A, 14B are also chosen based on reliability, intensity, temperature generation, and other factors. The illumination sources 14A, 14B are also redundant to further enhance reliability. As shown in FIG. 1, the redundant illumination sources 14A, 14B can be oriented at 90 degrees from each other with a "50-50" beam splitter 36 located near their center point to provide a constant source of illumination.

FIG. 1 further shows a plurality of lenses 16A, 16B, respectively associated with each of the illumination sources 14A, 14B. The lenses 16A, 16B are used to collect the light signal 34 from the illumination sources 14A, 14B and to focus the light signal 34 on a modulator or chopper wheel 18, described below. As shown, the lenses 16A, 16B are positioned to capture as much of the light signal 34 as possible from the illumination sources 14A, 14B. Additionally, a chopper-focusing lens 17 is used to focus as much of the light signal 34 as possible through the chopper wheel 18. The skilled artisan will instantly recognize the lenses 16A, 16B 17 are selected for focal length, position, material of construction and the like to enhance transmission (reduce loss) of the light signal 34. For example, in the design of the optical path, if the illumination sources 14A, 14B is a lamp, slight magnification or demagnification of the source is generally obtained at the sample W, depending on the ratios of the focal length, e.g., of the lens 16A to that placed after the illumination source 14A to collimate it. Ultimately, the image of the illumination source 14A on the sample W is directed toward the detectors 30, 32 as described below and again with some slight magnification or demagnification, depending on the ratios of the focal length, e.g., of the lenses 16A to that of, e.g., a lens 50 placed before the detector 30 to focus a reflected light 46 onto the detector 30. Thus, it should be understood that there is a relationship between the focal lengths of the lenses 16A, 16B that must be maintained in order to make sure the ultimate image of the source-excited region of the sample W that is formed on the detectors 30,32 is suited to the physical dimensions of the detectors 30,32.

The skilled artisan will further appreciate that the lenses 16A, 16B shown for example in FIG. 1 are plastic, Fresnel lenses well suited for use in an infrared (IR) region of about 1000 nanometers (nm) to about 3000 nm. However, the skilled artisan will understand that the lenses 16A, 16B are not limited to only plastic, Fresnel lenses and that other types of lenses and materials such as glass can be used for these lenses.

As further shown in FIG. 1, the chopper wheel 18 includes a plurality of alternating windows 38 and a plurality of alternating spokes 40. The alternating windows 38 and spokes 40 modulate the light signal 34 from about 50 Hertz (Hz) to about 5000 Hz to enable a plurality of photodetectors 52, 56 in the optical system 10 to perform properly, as will be further described below. As shown in this example, the chopper wheel 18 is a 10-window chopper wheel rotating at 40 Hz, which provides a chopped signal of 400 Hz. The number and arrangement of the windows 38 and spokes 40 and thus, the chopper frequency, are chosen based on several variables, including a rate of motion of the sample material W moving past the sampling window 13; a performance characteristic of the photodetectors 52,56 and amplification system; a predetermined sampling rate of the data collection and analysis system 10; physical properties of a chopper motor (not shown), control system (not shown), and the chopper wheel 18 (including material(s) of the windows 38).

More particularly, the number of windows 38 in the chopper wheel 18 can be adjusted to provide a suitable degree of signal modulation. In one aspect of the disclosure, the chopper wheel 18 has open windows 38 and black spokes 40, which block the light signal 34. In another aspect, different materials can be placed in the windows 38 to provide different spectral characteristics for the various windows 38. These window materials would be at least somewhat transmissive to the light signal 34. Moreover, the transmission characteristic of these windows 38 could be used as further spectral elements. The windows 38 can also contain multivariate optical elements (MOE) such as those described below with respect to a MOE 48 of the MOE detector 30.

FIG. 1 also shows a plurality of bandpass filters or spectral elements 20 located in a path of the light signal 34 after the light signal 34 has passed through the chopper wheel 18. As briefly discussed above, the spectral elements 20 are selected based on a desired application; i.e., to analyze a particular sample W. The spectral elements 20 are chosen so that the spectral region of illumination covers the desired range; i.e., related to a particular chemical material of interest. For example, if 1500-2000 nanometers (nm) of light wavelengths is the desired spectral region, the spectral elements 20 are selected to filter out wavelengths are not in that region. By way of further example but not of limitation, some suitable materials for use as the spectral elements 20 are listed in the following table.

TABLE 1

Properties of Select Infrared Transmitting Materials

| Material | Comments | SWL cm−1 | LWL cm−1 | RI | Solubility g/100 g | Hardness Kg/mm2 | MP ° C. | pH Range |
|---|---|---|---|---|---|---|---|---|
| AMTIR | SeAsGe glass, brittle | 11000 | 593 | 2.5 | 0 | 170 | 370 | 1-9 |
| BaF2 | Barium Fluoride | 66600 | 691 | 1.45 | 0.17 | 82 | 1280 | 5-8 |
| CaF2 | Calcium Fluoride | 79500 | 896 | 1.4 | 0.0017 | 158 | 1360 | 5-8 |
| CsI | Cesium Iodide, very hygroscopic, Somewhat Toxic | 42000 | 172 | 1.73 | 44 | 20 | 621 | NA |
| Diamond | Type IIa, strong IR absorbance between 2700-1800 cm−1, costly | 30000 | <2 | 2.4 | 0 | 5700 | 550 fp | 1-14 |
| Ge | Germanium, brittle, becomes opaque at elevated temperatures | 5500 | 432 | 4 | 0 | 780 | 936 | 1-14 |

TABLE 1-continued

Properties of Select Infrared Transmitting Materials

| Material | Comments | SWL cm−1 | LWL cm−1 | RI | Solubility g/100 g | Hardness Kg/mm2 | MP °C. | pH Range |
|---|---|---|---|---|---|---|---|---|
| KBr | Potassium Bromide, most widely used for mid-IR applications | 48800 | 345 | 1.52 | 53 | 6 | 730 | NA |
| KCl | Potassium Chloride | 55600 | 385 | 1.45 | 35 | 7 | 776 | NA |
| KRS-5 | Thallium Bromide/ Thallium Iodide, Extremely Toxic! | 17900 | 204 | 2.37 | 0.05 | 40 | 414 | 5-8 |
| NaCl | Sodium Chloride | 52600 | 457 | 1.49 | 36 | 18 | 801 | NA |
| Polyethylene | For Far-IR, swells with some organic solvents | 625 | <4 | 1.52 | 0 | | 110 | 1.5-14 |
| SiO2 | Silicon Dioxide | 50000 | 2315 | 1.53 | 0 | 460 | 1713 | 1-14 |
| Si | Silicon, strong IR absorbance between 624-590 cm−1 | 8900 | 624.30 | 3.41 | 0 | 1150 | 1420 | 1-12 |
| ZnS | Zinc Sulfide | 17000 | 690 | 2.2 | 0 | 240 | 1830 | 5-9 |
| ZnSe | Zinc Selenide | 15000 | 461 | 2.4 | 0 | 120 | 1526 | 5-9 |

Note:
To convert from wavenumber (cm−1) to wavelength (μm), divide 10,000 by the wavenumber; e.g., 5500 cm−1 is equivalent to 1.8 μm or 1800 nm.
SWL—Shortest wavelength for transmission, 1 mm, 50% transmission
LWL—Longest wavelength for transmission, 1 mm, 50% transmission
RI—Refractive Index, at relevant wavelength
MP—Melting point
pH - negative log of hydrogen ion concentration With reference now to both FIGS. 1 and 2, the light signal 34 exits the spectral elements 20 and reflects off a first mirror or turning mirror 24. It will be appreciated that although the turning mirror 24 is shown at an angle of about 45 degrees with the light signal 34 reflecting at this angle, the turning mirror 24 can be turned to any desired angle. As known to those skilled in the art, the turning mirror 24 can be a powered turning mirror powered by a battery, by electricity or the like. Further description of power sources and implementation with the turning mirror 24 is not necessary for one skilled in the art to understand this aspect of the disclosure. The skilled artisan will further appreciate that although the turning mirror 24 is shown as a unitary mirror, this and other exemplary embodiments of the disclosure can utilize multiple mirrors arranged in or adjustable to a variety of positions.

Figure 2:
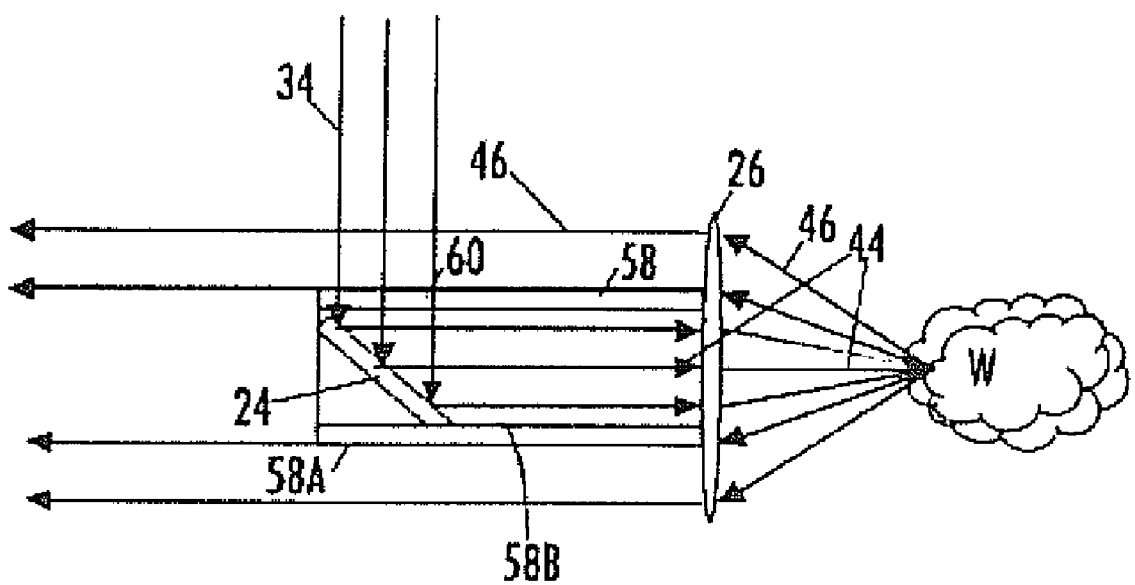
FIG. 2 is a schematic view of a concentric cavity as in FIG. 1 in accordance with a further aspect of the present disclosure.

As further shown in FIGS. 1 and 2, the filtered and reflected light signal 34 becomes a reflected light 44 after being reflected by the turning mirror 24. The reflected light 44 thus continues down the concentric sampling tube 22, briefly introduced above, in a direction of the sample W. As shown and further described below, the concentric tube 22 includes an inner annular region (also referred to as tube or chamber) 42A and an outer annular region 42B (also, tube or chamber). In this example, the reflected light 44 is reflected along the inner annular region 42A. It will be understood that the illumination sources 14A, 14B and the detectors 30, 32 are shown in an exemplary orientation and can be reversed. It will be further appreciated that the light signal 34 and the reflected light 44 are shown collimated for simplicity. However, the light signal 34 and the reflected light 44 may not be completely collimated because the illumination sources 14A, 14B can be extended rather than point sources.

The focusing lens 26 in FIGS. 1 and 2 is located near an end of the tube 22 proximate the sample W. As shown in this example, the end of the tube 22 is sealed with the transmissive window 13. The transmissive window 13 should be uniformly transmissive across wavelengths, but if it is not, the transmission characteristics of the transmissive window 13 are taken into account for the design of the system 10 and in particular the MOE 48. This embodiment may include an additional focusing lens 66, which can be solid or have one or more apertures as shown in FIG. 1. The additional focusing lens 66 is used to focus or collimate a carrier light 46, described below, in a direction of the tube 22.

As further shown in FIGS. 1 and 2, the focusing lens 26 focuses the reflected light 44 onto, into or near the sample W via the transmissive window 13. In this example, the reflected light 44 is focused with a focal point 0-5 mm into the sample W. In addition to isolating components of the optical analysis system 10 from an external environment, the transmissive window 13 further enables a mixing vessel or container C, which is being tested/sampled into, to remain intact. As shown in this example, a one-inch (inner diameter) Swagelok® brand connector 62, available from Swagelok Corporation, Solon, Ohio, is used to connect the optical analysis system 10 to the mixing vessel C. This arrangement permits the reflected light 44 to be sent down the tube 22 (inner region 42A), interact with the material of interest W, reflect back up the tube 22 (outer region 42B), and be directed to the detectors 30, 32 as further described below.

As most clearly shown in FIG. 2, a tube 58 defines an aperture 60 for passage of the light signal 34 in a direction of the turning mirror 24. Separation of the illumination and reflection light paths or signals 44, 46 can be further defined or separated by physically separating the inner and outer regions 42A, 42B employing the tube 58. Any minimal reduction in light return of the carrier light 46 described below (caused by physical occupation of a portion of the outer region 42B by the tube 58) is offset by improvement in the amount of backscattered radiation returned to the detectors 30, 32 without encountering the sample W.

More specifically, the tube 58 is used to reduce a non-zero background measurement. The non-zero background measurement can occur in an optical system when a small amount of scattered light is returned to a detector even when no sample is present. Some of the scattered light can be reflected from a window, and some can come from the lenses themselves.

FIG. 2 shows that the tube 58 placed around the mirror 24 before the lens 26. The tube 58 reduces background signals by separating the excitation and collection light paths 34, 46 to minimize "cross-talk". As shown, the tube 58 defines an aperture 60 for passage of the light signal 34 in a direction of the turning mirror 24. As further shown, a conical extension 58A of the tube 58 can be placed after the mirror 24 in a direction of the detector 30. A thickness of the tube 58 should be minimized.

Also shown in FIG. 2, the tube 58 can have specular interior and exterior surfaces as well as a highly reflective coating 58B, such as gold, applied by electrolysis deposition, evaporation or other thin film coating method. The coating 58B reflects rays 34, 46 that would ordinarily terminate at a surface of the tube 58 back into respective optical paths from which they came. An image of the illumination source 14A, 14B may be vignetted, but the "lost" light in the image is still focused to a spot within the zone illuminated by the illumination source 14A, 14B. Likewise, the returning light outside the tube 58 can be kept from being lost by traveling inside an outer tube with a specular reflecting surface (not shown, but surrounding the outer light path). This will keep light loss to a minimum while keeping the input and output paths relatively isolated from one another.

As introduced above, the reflected light 46 shown in FIGS. 1 and 2 travels back down the outer annular region 42A of the sampling tube 22, past the turning mirror 24. The light 46 reaches the beam splitter 28 (one of its operating positions shown in phantom). The beam splitter 28 divides the light 46 with a neutral or gray spectrum, sending some of the light 46 in a direction of the first or Multivariate Optical Element (MOE) detector through the MOE 48, briefly introduced above, and through a first lens 50 onto the photo detector 52, also briefly introduced above. The beam splitter 28 sends some other portion of the light 46 through a second lens 54 onto the other detector 56, also briefly introduced above.

As shown in the following table by example but not of limitation, some detectors suitable for use as the detectors 52,56 include:

TABLE 2

| Detector | Types[1] | Wave Range ($\lambda\mu$) | Detectivity $D^2$ | Cut Off Frequency ($H_z$) | Operating Temperature (K) |
|---|---|---|---|---|---|
| Pt-S | PV | 0.35-0.6 | 30 | $10^8$ | 295.0 |
| Si p-n PD | PV | 0.4-1.0 | 50 | $10^7$ | 295.0 |
| Si p-i-n PD | PV | 0.4-1.1 | 80 | $10^8$ | 295.0 |
| Si APD | PV | 0.4-0.8 | 80 | $10^{10}$ | 295.0 |
| Ge p-n PD | PV | 0.6-1.8 | 50 | $10^7$ | 295.0 |
| InSb p-n PD | PV | 3.0-6.2 | 8 | $5 \times 10^2$ | 77.0 |
| PbSnTe p-n PD | PV | 5.0-11.4 | >15-60 V/W | 10 | 77.0 |
| PbS | PC | 0.5-3.8 | 15.00 | 300 | 196.0 |
| PbSe | PC | 0.8-4.6 | 3.00 | $3 \times 10^3$ | 196.0 |
| PbTe | PC | 0.8-5.5 | 0.16 | $3 \times 10^3$ | 196.0 |
| p-InSb | PC | 2.0-6.7 | 2.00 | $2 \times 10^5$ | 77.0 |
| n-InSb | PC | 1.0-3.6 | 30.00 | $2 \times 10^6$ | 195.0 |
| PbSnTe | PC | 5.0-11.0 | 1.7 | $8 \times 10^5$ | 4.2 |
| CdHgTe | PC | 5.0-16.0 | 3.00 | $10^4$ | 4.2 |
| Ge:Au | PC | 2.0-9.5 | 0.02 | $10^4$ | 77.0 |
| Ge:Zn,Au | PC | 5.0-40.0 | 1.00 | $10^3$ | 4.2 |
| Ge:Cu | PC | 5.0-30.0 | 3.00 | $10^3$ | 4.2 |
| Si:Al | PC | 2.0-16.0 | 1.00 | $10^4$ | 27.0 |
| Si:Sb | PC | 2.0-31.5 | 1.80 | $10^4$ | 4.0 |
| ATGS | TC | 1-1000 | 0.030 | 10 | 295.0 |
| (Ba,Sr)TiO$_3$ | TC | 1-1000 | 0.011 | 400 | 295.0 |
| Si | — | 0.2-1.1 | — | — | — |
| Ge | — | 0.4-1.8 | — | — | — |
| InAs | — | 1.0-3.8 | — | — | — |
| InSb | — | 1.0-7.0 | — | — | — |
| InSb (77K) | — | 1.0-5.6 | — | — | — |
| HgCdTe (77K) | — | 1.0-25.0 | — | — | — |

Note 1:
PV—photo transistor type;
PC: photo conductive detector type;
TC: pyroelectric detector type
Note 2:
($10^{10}$ cmHz$^{1/2}$ W$^1$)

As further shown in FIG. 1, a gain mechanism 64 is in communication with the detectors 30, 32 and the MOE 48. The gain mechanism 64 weights a magnitude of the property of an orthogonal component of a portion of the carrier light 48 as described, for instance, by Myrick et al. in U.S. Pat. No. 6,198,531 B1 and in U.S. Pat. No. 6,529,276 B1 to Myrick.

As briefly introduced above the beam splitter 28 is not required in an alternative embodiment of the disclosure in which a signal from the sample W is analyzed using a PCR-type model in an off-line approach. This alternative embodiment and approach is useful, for instance, for studying signals independently. More particularly, a system substantially as described above but without the beam splitter 28 is used to take an integral of the light on a detector similar to the detector 30 described above. By analyzing frequency-dependent intensities, results similar to those of the foregoing embodiment are produced, although possibly with a relatively slower response time in the present embodiment.

Also, in an additional aspect of the disclosure as shown in FIG. 1, a system 68 using an electrochemical or chemometric model can be employed in conjunction with any of the foregoing embodiments to make similar or same measurements of the light 46 reflected from the sample W as the measurements described in the foregoing embodiments. By way of example but not of limitation, the system 68 may be one as described by Myrick et al. in PCT Application Number PCT/US2004/043742, based on U.S. Provisional Application No. 60/533,570, filed Dec. 31, 2003, which are incorporated herein by reference to these applications.

In addition to the reflectance mode described above, one or more optical analysis systems can operate in a transmission mode in conjunction with the foregoing embodiments. In such a case, light is directed (passes) through the sample W, e.g., a fluid sample, and collected on another side of the sample W to enable study of particle density in the fluid in conjunction with the chemical content described above. For instance, the system 10 can be configured to operate in transmission mode where the light is shone through the sample W to a similar detection system 110 as shown in FIG. 1 in phantom for clarity). Additionally, or alternatively, a mirrored surface 210 can be placed within the transmissive sample W to reflect the light back into the system 10.

Also in accordance with the present technology, an auto-calibration feature is provided for the various systems described herein. The auto-calibration feature may be implemented by various methods. For example, the system 10 as described above measures a first signal "A" corresponding to the signal from a detector through a multivariate optical element (MOE) and a second signal "B" corresponding to a reference signal from another detector. The ratio of these two signals may be used to measure the concentration of a chemical of interest. In order to maintain stability and/or reliability in the measurement, an auto-calibration process in accordance with the present subject matter may be implemented to confirm the signals A and B independently or the ratio of A and B.

The auto-calibration process according to the present technology may be performed according to several different methodologies. The following methods are exemplary of the possible methodologies and are not intended as limitations on the full range of methods that may be employed.

It will be recalled that a portion of the overall system includes a chopper wheel as shown in FIG. 1. Rotation of the chopper wheel modulates the light impinging on the sample and hence the photodetector. A first method of the auto-calibration process involves placing a single known material in one or more of the chopper windows. A second method of the auto-calibration process involves providing different known materials in several of the chopper windows. In accordance with the first and second methods, by having knowledge of the composition of the material(s) in the chopper windows, the signal coming from the detector can be determined. It should be appreciated that, in general, it is not a requirement of the present technology to provide a specific number of windows in the chopper wheel. By using multiple calibration materials in the chopper wheel, several calibration parameters in the control software can be set, confirmed, or verified, essentially one per calibration material.

A third calibration method of the auto-calibration process involves a movable mirror (see FIG. 1) positioned so that, either by turning or horizontal displacement, the light that is normally directed down a sampling tube would be directed toward the beam splitter and hence the detectors without encountering the sample. The mirror can be positioned so that the illumination light beam is directed down the sampling tube toward the sample focusing lens. During calibration, the mirror is turned toward a second position. In this second position, the light is directed from the illumination source and the chopper wheel to the beamsplitter and then to the detectors by way of the beam splitter.

In one embodiment of a movable mirror methodology, a mirror assembly is configured to move horizontally with a mirror angled to direct light down the sampling tube and a mirror angled to direct light toward the beamsplifter. During normal sampling, the mirror may be positioned in a first position and for calibration, the mirror would be moved.

It should be appreciated that it may be necessary to adjust the gain on the detectors to measure the light from this "bypass." Alternatively, calibration materials that transmit a lower amount of light can be chosen so that the detectors can be kept at the same gains used for measuring the sample. Detectors provide an increased output signal dependent upon the amount of light impinging on them. As such, there is a preferred operating region for the detectors and subsequent amplification of the signal such that the final output does vary with the amount of impinging light. For instance, there are levels of light that are too low to produce a reliable output signal. In addition, there are levels of light that are too great and overload the detection system. At these high light levels, changes in the amount of light do not change the output signal. The preferred mode of operation is where the amount of light is in the range where there is a good correlation between the amount of light and the output signal of the detector system.

In accordance with the present auto-calibration technology, light is directed from the illumination sources to the detectors without interacting with the sample. Depending upon the type of sample being analyzed and the transmission characteristic of the light path between the illumination source, the sample, and the detectors, there can be a range of signals returned to the detector. As an example, the light path could include a fiber optic probe or the sample could be a powder being measured in a reflectance mode. In both of these examples, the amount of light returning to the detectors during normal sampling could be significantly less than the amount of light following the by-pass or calibration route to the detectors. In an exemplary configuration, light transmission through a sample may be reduced from 50-99.9%. Thus, in order to enable the detector and amplification system to operate over a useful range, some attenuation of the signal in the calibration elements may be needed.

In accordance with the present auto-calibration technology, a fourth calibration methodology involves providing an element in a chopper wheel that turns the light path slightly in addition to having a known spectral characteristic. Light can be directed to a reflective surface that sends light to a beam splitter and then to detectors. A particular aspect to this embodiment is that it allows for a continuous or real time check of the instrument calibration with each rotation of chopper wheel. In accordance with this method, a stationary mirror assembly allows the un-deflected beam to pass to the sample for sample measurements and the deflected beam to be directed toward the detection system without passing through or encountering the sample.

The present subject matter may be better understood from the following tests and examples.

EXAMPLE I

System I

A first breadboard system was constructed and used to test a mixture of powders.
System I Components:
Illumination: 20 W Gilway lamp
Spectral elements: 5 mm deuterium oxide ($D_2O$), 5 mm Germanium
Optical window: fiber optic probe
Detector: InAr detector from Judson
MOE: specific to test
Procedure and Results of Static Testing Using System 1:
A powdered sample with a known composition was placed in a dish and the fiber optic probe was placed in contact with the powder. The output of the detectors was monitored and recorded.

EXAMPLE II

System II

A system similar to the optical analysis system 10 shown in the figures was constructed and used to make static measurements on aspirin/lactose.
System II Components:
Illumination: 20 W Gilway lamp
Spectral elements: 5 mm D2O, 5 mm Germanium
Optical window: none
Detector: PbS detector from New England Photoconductor
MOE: specific to test conditions.
Procedure and Results of Static Testing Using System II:
A powdered sample with a known composition was placed in a dish and the system light beam was focused on the powder. The output of the detectors was monitored and recorded. Aspirin/lactose samples covering the range of 100% aspirin to 100% lactose were tested.

EXAMPLE III

System III

A system similar to the optical analysis system 10 shown in the figures was constructed and used to make dynamic measurements on aspirin/lactose.

System III Components:
Illumination: 20 W Gilway lamp
Spectral elements: 5 mm D2O, 5 mm Germanium
Optical window: sapphire window
Detector: PbS detector from New England Photoconductor
MOE: specific to test conditions.

Procedure and Results of Dynamic Testing Using System III:

The Aspirin/Lactose testing was made on a mixer bowl containing lactose and the system measured as aspirin was added to the system and mixed. Specifically, lactose powder was placed in the bowl of a mixer and the measurement system was attached the bowl using a Swagelok® brand fitting. A sapphire window was used to contain the powder in the bowl and allow the system to interrogate the powder. With the mixer turning, known amounts of aspirin were added and the system output signal was monitored and recorded. Aspirin was added in several allotments to about 37% final aspirin concentration.

EXAMPLE IV

System IV

A system similar to the optical analysis system 10 shown in the figures was constructed and used to make static measurements on aspirin/lactose.

System IV Components:
Illumination: 5 W Gilway lamp
Spectral elements: 5 mm D2O, 5 mm Germanium
Optical window: none
Detector: PbS detector from New England Photoconductor
MOE: specific to test conditions.

Procedure and Results of Dynamic Testing Using System III:

Similar to the examples above.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

That which is claimed is:

1. A method of determining information carried by light using a multivariate optical analysis system, the method comprising:
   filtering a source light through a spectral element;
   reflecting the filtered light through a first region of a cavity in a first direction of a sample to be measured, the cavity including an element forming a first aperture for passage of the reflected filtered light, the element defining a second aperture having no reflected filtered light passing therethrough;
   focusing the reflected light proximate to the sample;
   reflecting the focused light from the sample through the second aperture in a second direction of a beamsplitter, the light being reflected from the sample, the reflected light carrying information about the sample;
   splitting the light from the second aperture with the beamsplitter into a first light and a second light;
   optically extracting the information of the first light with an optical element into an orthogonal component;
   directing the first light extracted by the optical element onto a first photodetector to measure a first signal;
   directing the second light onto a second photodetector to measure a second signal; and
   comparing the first signal to the second signal to determine a property of the sample.

2. The method as in claim 1, wherein the light is focused in the sample, the light having a focal point of about 0 mm to about 5 mm in the sample.

3. The method as in claim 1, wherein the beamsplitter is a 50/50beamsplitter.

4. The method as in claim 1, further comprising modulating the light.

5. The method as in claim 1, further comprising modulating the light from about 50 Hz to about 5000 Hz.

6. The method as in claim 1, further comprising controlling a spectral range of the light source, the spectral element having a predetermined transmission characteristic for controlling the spectral range.

7. The method as in claim 1, further comprising measuring a concentration of the sample using a ratio of the first light and the second light.

8. The method as in claim 1, further comprising monitoring the first light, the second light or combinations thereof to assess particle segregation of the sample.

9. The method as in claim 1, further comprising monitoring the first light, the second light or combinations thereof to assess density of the sample.

10. The method as in claim 1, further comprising monitoring the first light, the second light or combinations thereof to assess an effect of particle size in the sample.

11. The method as in claim 1, further comprising monitoring the first light, the second light or combinations thereof to measure a chemical in the sample.

12. The method as in claim 1, further comprising monitoring the first light, the second light or combinations thereof to measure homogeneity of the sample.

13. The method as in claim 1, further comprising preparing a chemometric model of the light reflected from the sample.

14. The method of claim 1, further comprising:
   determining a plurality of orthogonal components of the first light, wherein each of the components has a predetermined shape with respect to a property of the first light of the sample carrying light that varies over a predetermined wavelength range;
   determining respective weightings for the orthogonal components so that the magnitude of the orthogonal components in the first light, weighted by the weightings, is proportional to information present in the first light in a predetermined relationship;
   disposing an optical filter to receive the first light, the optical filter configured to optically filter the orthogonal components;
   disposing the second photodetector to receive the second light;
   detecting the property of the first light filtered by the optical filter;
   receiving the second light with the second photodetector; and
   analyzing the sample in real time by comparing the property of the first light to information in the second light.

15. An optical analysis system for determining information carried by light, the optical analysis system comprising:
- a light source being configured to radiate a first light along a first ray path;
- a modulator disposed in the first ray path, the modulator being configured to modulate the first light to a desired frequency;
- a spectral element disposed proximate the modulator, the spectral element being configured to filter the first light for a spectral range of interest of a sample;
- a cavity in communication with the spectral element, the cavity being configured to direct the first light in a direction of the sample, the sample reflecting the first light as a second light, the cavity being further configured to direct the second light and comprising a geometrical element to form a first aperture for the first light different from a second aperture for the second light, having no first light passing through the second aperture;
- a beamsplitter being configured to split the second light into a first beam and a second beam;
- an optical element disposed to receive the first beam, the optical element being configured to optically extract information carried by the first beam into at least one orthogonal component of the first beam;
- a first detector in communication with the optical element to measure a property of the orthogonal component to measure the information; and
- a second detector being configured to receive the second beam for comparison of the property of the orthogonal component to the second beam.

16. The optical analysis system as in claim 15, wherein the cavity includes a first region and a second region, the first region being configured to direct the second light in a direction of the beamsplitter, the second region being configured to direct the first light in a direction of the sample.

17. The optical analysis system as in claim 15, wherein the optical element is a multivariate optical element.

18. The optical analysis system as in claim 15, further comprising a gain in communication with at least one of the optical element, the first detector and the second detector, the gain being configured to weight a magnitude of the property of the light orthogonal component.

19. The optical analysis system as in claim 15, further comprising a mirror disposed proximate the cavity, the mirror being to direct the first light in the cavity in the direction of the sample.

20. An optical analysis system for determining information carried by light, the optical analysis system comprising:
- a light source being configured to radiate a first light along a first ray path;
- a cavity disposed along said first ray path, the cavity being configured to direct the first light in a direction of the sample, the sample reflecting the first light as a second light, the cavity being further configured to direct the second light and comprising a geometrical element to form a first aperture for the first light different from a second aperture for the second light, having no first light passing through the second aperture;
- a beamsplitter being configured to split the second light into a first beam and a second beam;
- an optical element disposed to receive the first beam, the optical element being configured to optically extract at least one orthogonal component of the first beam;
- a first detector in communication with the optical element to measure a property of the orthogonal component; and
- a second detector configured to receive the second beam.

21. The system of claim 20, wherein the optical filter is a multivariate optical filter;
- said system further comprising a spectrograph disposed relative to the light source and the filter such that the spectrograph directs the light from the light source to the filter, the spectrograph being configured to separate the light into a spectrum.

22. The system of claim 20, further comprising a gain mechanism in communication with said first and second detectors, said gain mechanism configured for comparison of the property of the orthogonal component to the second beam, 23. The system of claim 20, further comprising a modulator disposed in the first ray path, the modulator being configured to modulate the first light to a desired frequency; and
- a spectral element disposed proximate the modulator, the spectral element being configured to filter the first light for a spectral range of interest of a sample.

24. A method of determining information carried by light using a multivariate optical analysis system, the method comprising:
- filtering a source light through a spectral element;
- reflecting the filtered light through a first region of a cavity in a first direction of a sample to be measured, the cavity defining a separate second region within the cavity;
- focusing the reflected light proximate to the sample;
- reflecting the focused light from the sample through the second region in a second direction of a beamsplitter, the light being reflected from the sample, the reflected light carrying information about the sample;
- separating the light reflected from the sample and the filtered light in the second region;
- splitting the light reflected from the sample with the beamsplitter into a first light and a second light;
- optically extracting the information of the first light with an optical element into an orthogonal component;
- directing the first light extracted by the optical element onto a first photodetector to measure a first signal;
- directing the second light onto a second photodetector to measure a second signal; and
- comparing the first signal to the second signal to determine a property of the sample; and
- auto-calibrating the multivariate optical analysis system using a first signal corresponding to the signal from a detector through an optical element and a second signal corresponding to a reference signal from a separate detector.

25. The optical analysis system of claim 15 wherein the geometrical element is a tube.

26. The method of claim 1 wherein the optical element is a multivariate optical element.

27. The method as in claim 24, wherein the sample comprises gasoline.

28. The method of claim 24, wherein the optical element comprises a multivariate optical element.

29. The method of claim 28, wherein the multivariate optical element comprises principal components related to an octane rating of the gasoline sample.

30. The method as in claim 24, wherein the light is focused in the sample, the light having a focal point of about 0 mm to about 5 mm in the sample.

31. The method as in claim 24, wherein the beamsplitter is a 50/50 beamsplitter.

32. The method of claim 24, further comprising modulating the light.

33. The method as in claim 24, further comprising modulating the light from about 50 Hz to about 5000 Hz.

34. The method as in claim 24, further comprising controlling a spectral range of the light source, the spectral element having a predetermined transmission characteristic for controlling the spectral range.

35. The method as in claim 24, further comprising measuring a concentration of the sample using a ratio of the first light and the second light.

36. The method as in claim 24, further comprising monitoring the first light, the second light or combinations thereof to assess particle segregation of the sample.

37. The method as in claim 24, further comprising monitoring the first light, the second light or combinations thereof to assess density of the sample.

38. The method as in claim 24, further comprising monitoring the first light, the second light or combinations thereof to assess an effect of particle size in the sample.

39. The method as in claim 24, further comprising monitoring the first light, the second light or combinations thereof to measure a chemical in the sample.

40. The method as in claim 24, further comprising monitoring the first light, the second light or combinations thereof to measure homogeneity of the sample.

41. The method as in claim 24, further comprising preparing a chemometric model of the light reflected from the sample.

* * * * *